(12) United States Patent
Scavone et al.

(10) Patent No.: US 6,979,438 B2
(45) Date of Patent: Dec. 27, 2005

(54) ANTIPERSPIRANT COMPOSITIONS CONTAINING PETROLATUM

(75) Inventors: Timothy Alan Scavone, Loveland, OH (US); Kelly Lynn Cassiere, Reading, OH (US); Keith David Ertel, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 209 days.

(21) Appl. No.: 10/057,182

(22) Filed: Jan. 25, 2002

(65) Prior Publication Data

US 2003/0152539 A1 Aug. 14, 2003

(51) Int. Cl.$^7$ ............... A61K 7/32; A61K 7/34; A61K 7/36; A61K 7/38; A61K 7/00
(52) U.S. Cl. ............... 424/65; 424/66; 424/67; 424/68; 424/401
(58) Field of Search ............... 424/401, 65, 66, 424/67, 68

(56) References Cited

U.S. PATENT DOCUMENTS

| | | |
|---|---|---|
| 5,176,903 A | 1/1993 | Goldberg et al. |
| 5,194,262 A | 3/1993 | Goldberg et al. |
| 5,292,530 A | 3/1994 | McCrea et al. |
| 5,401,870 A | 3/1995 | Raleigh et al. |
| 5,455,025 A | 10/1995 | Pereira et al. |
| 5,547,661 A | 8/1996 | Sun et al. |
| 5,626,856 A | 5/1997 | Berndt |
| 5,662,937 A | 9/1997 | McCuaig |
| 5,744,146 A | 4/1998 | Peters et al. |
| 5,776,494 A | 7/1998 | Guskey et al. |
| 5,843,414 A | 12/1998 | Hilvert et al. |
| 5,846,520 A | 12/1998 | Guskey et al. |
| 5,849,276 A | 12/1998 | Guskey et al. |
| 5,902,571 A * | 5/1999 | Putman et al. ............... 424/65 |
| 5,932,199 A | 8/1999 | Esser |
| 5,945,095 A | 8/1999 | Mougin et al. |
| 5,958,386 A | 9/1999 | Sawin et al. |
| 5,976,514 A | 11/1999 | Guskey et al. |
| 6,074,672 A | 6/2000 | Dobkowski et al. |
| 6,113,891 A | 9/2000 | Burdick et al. |
| 6,187,300 B1 | 2/2001 | Motley et al. |
| 6,280,752 B1 | 8/2001 | Panin |

FOREIGN PATENT DOCUMENTS

| | | |
|---|---|---|
| EP | 0061701 A2 | 10/1982 |
| EP | 0872248 A2 | 10/1998 |
| WO | WO 89/02264 | 3/1989 |
| WO | WO 99/51192 | 10/1999 |
| WO | WO 00/41528 | 7/2000 |

\* cited by examiner

*Primary Examiner*—Shengjun Wang
(74) *Attorney, Agent, or Firm*—William I. Winter; Jack Oney; Vladimir Vitenberg

(57) ABSTRACT

Disclosed are antiperspirant compositions comprising (a) from about 0.1% to about 30% by weight of an antiperspirant active; (b) from about 0.05% to about 0.95% by weight of petrolatum; (c) from about 10% to about 99% by weight of a liquid carrier; and (d) from about 0.1% to about 30% by weight of a suspending agent. The compositions provide a consumer perceived improvement in antiperspirant efficacy and product wash-off when the compositions are formulated with petrolatum within the above-described concentration ranges.

21 Claims, No Drawings

ANTIPERSPIRANT COMPOSITIONS CONTAINING PETROLATUM

TECHNICAL FIELD

The present invention relates to antiperspirant compositions that contain selectively small concentrations of petrolatum for improved wash-off and antiperspirant efficacy.

BACKGROUND OF THE INVENTION

Many different antiperspirant products are known for use in controlling or inhibiting underarm perspiration wetness and odor. These products are available in a variety of product forms such as solid sticks, soft solids or creams, roll-on liquids and aerosol or non-aerosol sprays. Most of these products have a base formula that contains an antiperspirant active such as an aluminum and or zirconium salt, a suspending or thickening agent, and a suitable liquid carrier.

Most antiperspirant products are formulated to provide a good skin cosmetics and skin feel, in balance with antiperspirant efficacy in controlling under wetness and malodor. Many ingredients used in antiperspirant products have at least some negative impact on antiperspirant efficacy, but are nonetheless formulated into the products to provide the consumer with desirable application cosmetics, product substantivity, and skin feel. For example, many antiperspirant products contain hydrophobic materials that help provide for smooth product application and substantivity on the underarm. Many of these hydrophobic materials, however, are hydrocarbon-based materials that tend to inhibit the release of antiperspirant active after application and thus inhibit antiperspirant efficacy. And because these hydrophobic materials are water-insoluble and highly substantive, they can be difficult to wash-off prior to the next application. Examples of such hydrocarbon-based materials include mineral oil, petrolatum, and similar other materials.

It has now been found that petrolatum can be added to antiperspirant products at low concentrations to provide a consumer perceived improvement in antiperspirant efficacy and wash-off performance. Although it is known that petrolatum can actually hamper wash-off and antiperspirant efficacy, it was found that petrolatum when used at concentrations ranging from about 0.05% to about 0.95% by weight of the composition actually provides a consumer-perceived improvement in wash-off performance and antiperspirant efficacy. Although the use of petrolatum is known for use in some antiperspirant products, Applicants are not aware of any formulation that specifically contains petrolatum at such concentrations, or that the use of such low petrolatum concentrations will actually enhance consumer perception of wash-off performance and antiperspirant efficacy.

It therefore an object of the present invention to provide antiperspirant compositions and methods of application that deliver consumer-perceived improvement in wash-off performance and antiperspirant efficacy, and further to provide such compositions and methods of application directed to the selected use of low petrolatum concentrations.

SUMMARY OF THE INVENTION

The present invention is directed to antiperspirant compositions and methods of using the compositions, wherein the compositions comprise (a) from about 0.1% to about 30% by weight of an antiperspirant active; (b) from about 0.05% to about 0.95% by weight of petrolatum; (c) from about 0.1% to about 35% by weight of a suspending or thickening agent, and (d) from about 10% to about 99% by weight of a liquid carrier.

It has been found that antiperspirant compositions containing petrolatum, a material that was previously known for inhibiting product wash-off and antiperspirant efficacy, can now be formulated to deliver consumer-perceived improvement in product wash-off and antiperspirant efficacy, provided that the petrolatum is formulated at relatively low concentrations of from about 0.05% to about 0.95%.

DETAILED DESCRIPTION OF THE INVENTION

The antiperspirant compositions of the present invention comprise as essential components an antiperspirant active, petrolatum, a suspending agent, and a liquid carrier. Each of these essential components and other key characteristics of the present invention are described hereinafter in more detail.

The term "anhydrous" as used herein refers to compositions or materials, including the preferred anhydrous embodiments of the present invention, that contain less than about 5%, more preferably less than about 3%, even more preferably less than about 1%, most preferably zero percent, by weight of free or added water, other than the water of hydration typically associated with any particulate solids prior to formulation.

The term "ambient conditions" as used herein refers to surrounding conditions under about one (1) atmosphere of pressure, at about 50% relative humidity, and at about 25° C., unless otherwise specified. All values, amounts and measurements described herein are obtained under ambient conditions unless otherwise specified.

The term "volatile" as used herein refers to those materials that have a measurable vapor pressure at 25° C. Such vapor pressures will typically range from about 0.01 mmHg to about 6 mmHg, more typically from about 0.02 mmHg to about 1.5 mmHg, and have an average boiling point at one (1) atmosphere of pressure (atm) of less than about 250° C., more typically less than about 235° C. at one (1) atm. Conversely, the term "non volatile" refers to those materials that are not "volatile" as defined herein.

The antiperspirant compositions and methods of the present invention can comprise, consist of, or consist essentially of the essential elements and limitations of the invention described herein, as well as any additional or optional ingredients, components, or limitations known or otherwise effective for use in such compositions.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Petrolatum

The antiperspirant compositions of the present invention comprise petrolatum at a relatively low concentration selected from the range of from about 0.05% to about 0.95%, preferably from about 0.3% to about 0.8%, more preferably from about 0.4% to about 0.7%, by weight of the composition.

It has been found that selectively low concentrations of petrolatum in the antiperspirant compositions of the present invention provide antiperspirant efficacy and wash-off benefits, even though petrolatum and other similar hydrocarbon materials are generally known for inhibiting antiperspirant efficacy and wash-off. It has been found that such is not the case for petrolatum, provided that it is formulated with the selectively low petrolatum concentrations described above.

The petrolatum for use in the composition is preferably a semi-solid under ambient conditions, but can be formulated as a liquid, semi-solid, or solid within the antiperspirant composition. The petrolatum can be derived from fractional distillation of still residues from the steam distillation of paraffin-based petroleum, or from steam-reduced crude oils from which the light fractions have been removed. Petrolatum grades include Natural grade which is generally made in accordance with the above-described derivation; Artificial grade which is generally made by mixing heavy petroleum lubricating oil with a low melting point wax; U.S.P (United States Pharmacopia) grade or white petrolatum; N.F. (National Formulary) grade or yellow petrolatum; and F.C.C. grade which includes both U.S.P. and N.F. grades.

The petrolatum for use in the compositions of the present invention is preferably U.S.P. white petrolatum. Especially preferred are petrolatums containing relatively low levels of alkyl chain lengths having less than 26 carbon atoms, one example of which is Witco Super White Protopet, a U.S.P. white petrolatum distinguished by its higher saybolt viscosity @ 210° F. (method ASTM D-445) of 60 (SUS units). By contrast, typical mineral genies have a saybolt viscosity @ 210° F. of 35, and medium viscosity petrolatum has a saybolt viscosity @ 210° F. of 55. Thus, it is preferred that a cut of petrolatum is used which has saybolt viscosity greater than 55.

It is important that the petrolatum concentrations be selected within the range of from about 0.05% to about 0.95% by weight of the composition, although for selected petrolatum grades or cuts that inherently have a less greasy skin feel, petrolatum concentrations can be formulated above about 1.0%, typically from about 1.0% to about 3%, but preferably less than 2%, most preferably less than 0.95%, by weight of the composition. These petrolatum materials with improved skin feel benefits even at slightly higher concentrations can also be characterized as those having a saybolt viscosity of greater than about 55. A non-limiting example of petrolatum grades having a less greasy skin feel, and which can be formulated at higher but less preferred concentrations, include White Petrolatum available from Witco as Superwhite Protopet cut (viscosity 60 SUS).

Antiperspirant Active

The antiperspirant compositions of the present invention comprise an antiperspirant active suitable for application to human skin. The concentration of the active should be sufficient to provide the desired perspiration wetness or odor control from the formulation selected.

The antiperspirant compositions of the present invention preferably comprise antiperspirant active at concentrations ranging from about 0.1% to about 30%, more preferably from about 5% to about 30%, by weight of the composition. These weight percentages are calculated on an anhydrous metal salt basis exclusive of water and any complexing agents such as glycine, glycine salts, or other complexing agents. The antiperspirant active can be solubilized or solid, but is preferably a solid. The antiperspirant active as formulated in the composition is preferably in the form of dispersed particulate solids having a preferred average particle size or diameter of less than about 100 $\mu$m, preferably from about 1 $\mu$m to about 40 $\mu$m.

The antiperspirant active for use in the antiperspirant compositions of the present invention include any compound, composition or other material having antiperspirant activity. Preferred antiperspirant actives include astringent metallic salts, especially inorganic and organic salts of aluminum, zirconium and zinc, as well as mixtures thereof. Particularly preferred are aluminum-containing and/or zirconium-containing salts or materials, such as aluminum halides, aluminum chlorohydrate, aluminum hydroxyhalides, zirconyl oxyhalides, zirconyl hydroxyhalides, and mixtures thereof.

Preferred aluminum salts for use in the anhydrous antiperspirant embodiments of the present invention include those which conform to the formula:

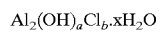

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the anhydrous antiperspirant embodiments of the present invention include those which conform to the formula:

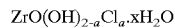

$$ZrO(OH)_{2-a}Cl_a \cdot xH_2O$$

wherein a is from about 1.5 to about 1.87; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorohydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

Antiperspirant actives suitable for use in the compositions include aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered, and combinations thereof.

Suspending Agent

The antiperspirant compositions of the present invention comprise a suspending or thickening agent, preferably a solid suspending or thickening agent, to help provide the compositions with the desired viscosity, rheology, texture and/or product hardness, or to otherwise help suspend any dispersed solids or liquids within the composition.

The term "suspending agent" as used herein, unless otherwise specified, means any material known or otherwise effective in providing suspending, gelling, viscosifying, solidifying and/or thickening properties to the composition or which otherwise provide structure to the final product form. These suspending agents include gelling agents, and polymeric or nonpolymeric or inorganic thickening or viscosifying agents. Such materials will typically be solids under ambient conditions and include organic solids, silicone solids, crystalline or other gellants, inorganic particulates such as clays or silicas, or combinations thereof.

The concentration and type of suspending agent selected for use in the antiperspirant compositions will vary depending upon the desired product hardness, rheology, formulation (e.g., antiperspirant formulation or deodorant formulation) and/or other related product characteristics. For most suspending agents suitable for use herein, the total suspending agent concentration ranges from about 0.1% to about 40%, more typically from about 0.1% to about 35%, by weight of the composition. Suspending agent concentrations will tend to be lower for liquid embodiments (e.g., aerosols, roll-ons, etc) and higher for semi-solid (e.g., soft solids or creams) or solid stick embodiments.

Non limiting examples of suitable suspending agents include hydrogenated castor oil (e.g., Castorwax MP80, Castor Wax, etc.), fatty alcohols (e.g., stearyl alcohol), solid paraffins, triglycerides and other similar solid suspending esters or other microcrystalline waxes, silicone and modified silicone waxes. Non limiting examples of optional suspending agents suitable for use herein are described in U.S. Pat. No. 5,976,514 (Guskey et al.), U.S. Pat. No. 5,891,424 (Bretzler et al.), which descriptions are incorporated herein by reference.

Other suitable suspending agents include silicone elastomers at concentrations ranging from about 0.1% to about 10%, by weight of the composition. Non-limiting examples of such silicone elastomer materials suitable for use as a suspending agent herein are described in U.S. Pat. No. 5,654,362 (Schulz, Jr. et al.); U.S. Pat. No. 6,060,546 (Powell et al.) and U.S. Pat. No. 5,919,437 (Lee et al.), which descriptions are incorporated herein by reference.

Carrier Liquid

The antiperspirant compositions of the present invention comprise a carrier liquid at concentrations ranging from about 10% to about 99%, preferably from about 20% to about 70%, by weight of the composition. Such concentrations will vary depending upon variables such as product form, desired product hardness, selection of other ingredients in the composition, and so forth. The carrier liquid for use in the composition can be any aqueous or anhydrous liquid that is known for use in personal care applications or is otherwise suitable for topical application to the skin. Anhydrous carriers are preferred.

The carrier liquid preferably comprises a volatile silicone liquid, which may include cyclic, linear and/or branched chain silicones. The concentration of volatile silicone in the antiperspirant composition of the present invention preferably ranges from about 5% to about 80%, preferably from about 20% to about 60%, more preferably from about 30% to about 60%, by weight of the composition. The volatile silicone is preferably a cyclic silicone having from about 3 to about 7, more preferably from about 5 to about 6, silicon atoms. Most preferred are those that conform to the formula:

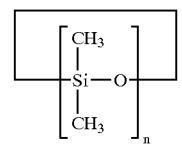

wherein n is from about 3 to about 7, preferably from about 5 to about 6, most preferably 5. These volatile cyclic silicones generally have a viscosity of less than about 10 centistokes. Suitable volatile silicones for use herein include, but are not limited to, Cyclomethicone D5 (commercially available from G.E. Silicones); Dow Corning 344, and Dow Corning 345 (commercially available from Dow Corning Corp.); and GE 7207, GE 7158 and Silicone Fluids SF-1202 and SF-1173 (available from General Electric Co.). Non limiting examples of suitable volatile silicones are described in Todd et al., "Volatile Silicone Fluids for Cosmetics", Cosmetics and Toiletries, 91:27–32 (1976), which descriptions are incorporated herein by reference.

The liquid carrier may comprise a non-volatile silicone liquid, preferred concentrations of which range from about 1% to about 35%, more preferably from about 5% to about 30%, by weight of the composition. The non volatile silicone carrier is preferably a liquid at or below human skin temperature, or otherwise in liquid form within the anhydrous antiperspirant composition during or shortly after topical application. Preferred are those nonvolatile liquid silicones that conform to either of the formulas:

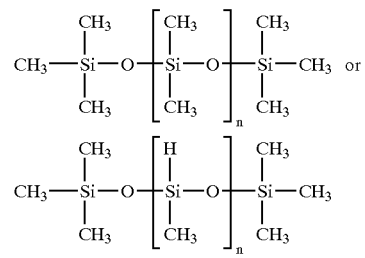

wherein n is sufficiently large to provide a viscosity of up to about 100,000 centistokes, preferably less than about 500 centistoke, more preferably from 10 centistoke to about 200 centistoke, even more preferably from 10 centistoke to about 50 centistoke, as measured under ambient conditions. Specific non limiting examples of suitable non volatile, linear, silicone carriers include Dow Corning 200, hexamethyldisiloxane, Dow Corning 225, Down Corning 1732, Dow Corning 5732, Dow Corning 5750 (available from Dow Corning Corp.); and SF-96, SF-1066 and SF18(350) Silicone Fluids (available from G.E. Silicones).

Many other carrier liquids known for use in personal care products can be used in the antiperspirant compositions, alone or in combination with other carrier liquids including those described in more detail herein. Many such other carrier liquids are disclosed in U.S. Pat. No. 6,013,248 (Luebbe et al.) and 5,968,489 (Swaile et al.), which descriptions are incorporated herein by reference.

Optional Ingredients

The antiperspirant compositions of the present invention may further comprise any optional ingredient that is known for use in antiperspirants and deodorant products or other personal care products, or which is otherwise suitable for topical application to human skin.

Non limiting examples of optional ingredients include dyes or colorants, emulsifiers, perfumes, propellants, deodorant perfumes, antimicrobial or other deodorant materials, preservatives, vitamins, non-vitamin nutrients, emollients, coupling agents or other solvents, surfactants, processing aides such as viscosity modifiers, wash-off aids, and so forth. Examples of such optional materials are described in U.S. Pat. No. 4,049,792 (Elsnau); U.S. Pat. No. 5,019,375 (Tanner et al.); and U.S. Pat. No. 5,429,816 (Hofrichter et al.); which descriptions are incorporated herein by reference.

Methods of Manufacture

The antiperspirant compositions of the present invention may be prepared by any known or otherwise effective technique suitable for formulating the desired antiperspirant product form.

Antiperspirant solid and semi-solid embodiments of present invention can be formulated, for example, by mixing volatile and nonvolatile silicone carrier liquids (or any other desired anhydrous carrier liquid) under ambient conditions, or under conditions sufficient to render the admixture fluid or liquid, and then adding any suspending agents to the mixture and heating the resulting mixture sufficiently to liquefy the added suspending agents, e.g., approximately 85° C. for many wax solids, and form a single phase liquid. Antiperspirant active and other water-soluble solids (e.g. solid pantothenate salts) are then typically added to and dispersed throughout the heated, single-phase liquid before allowing the resulting combination to cool to approximately 78° C., at which point perfumes and similar other materials (if any) are mixed into the combination, which is then cooled to just above the solidification point of the suspending agent (e.g., typically about 60° C.) and then poured into dispensing packages and allowed to solidify under ambient conditions.

Antiperspirant liquid embodiments of the present invention can be formulated, for example, by combining an anhydrous carrier liquid with a suitable suspending agent and activator for the suspending agent and allowing the combination to thicken to the desired viscosity before adding the antiperspirant active and other water-soluble solids with agitation. The resulting mixture is subjected to shear in a suitable homogenizer to achieve the desired concentrate viscosity. For aerosol liquid embodiments, the resulting liquid is then packaged into aerosol containers with an appropriate propellant in a concentrate to propellant ratio suitable for the propellant system selected.

Other suitable methods of making antiperspirant compositions are known and described in the antiperspirant art, and can be used to make the antiperspirant compositions of the present inventions. For solid antiperspirant embodiments, such methods include those described in U.S. Pat. No. 4,822,603 (Farris et al.) and U.S. Pat. No. 4,985,238 (Tanner et al.). For aerosol antiperspirant embodiments, such methods include those described in U.S. Pat. No. 6,136,303 (Ruebusch et al.); U.S. Pat. No. 4,904,463 (Johnson et al.) and U.S. Pat. No. 4,840,786 (Johnson et al.) For soft solid or cream embodiments, such methods are described in U.S. Pat. No. 5,902,571 (Putman et al.) and U.S. Pat. No. 5,902,570 (Bretzler et al.). All such method descriptions in the above-identified patent publications are incorporated herein by reference.

Method of Use

The antiperspirant compositions of the present invention may be applied topically to the axilla or other area of the skin in an amount effective to treat or reduce perspiration wetness and or malodor. The composition is preferably applied in an amount ranging from about 0.1 gram to about 20 grams, more preferably from about 0.1 gram to about 10 grams, even more preferably from about 0.1 gram to about 1 gram, to the desired area of the skin. The compositions are preferably applied one to two times daily, preferably once daily, to achieve effective antiperspirant and malodor control.

The antiperspirant compositions of the present invention can be formulated in a variety of product forms and then applied to the axilla or other area of the skin in the manner described herein, such variety product forms including solids (e.g., sticks), semi-solids (e.g., lotions, creams, soft solids), or liquids (e.g. aerosols, non-aerosol sprays, roll-ons, porous dome liquids).

The above-described are methods of the present invention, and can also be directed to methods of improving antiperspirant efficacy, said method comprising the topical underarm application of the compositions of the present invention, in accordance with the above-described methods.

The above-described methods of the present invention are also directed to methods of improving wash-off of the antiperspirant composition, said method comprising the topical underarm application of the compositions of the present invention, in accordance with the above-described methods.

EXAMPLES

The following non-limiting examples described in Tables 1–5 illustrate specific embodiments of the antiperspirant compositions of the present invention, including methods of manufacture and use. Each of the exemplified compositions is applied topically to the axilla area of the skin, in accordance with the methods of use described herein, and provide consumer-perceived improvements in antiperspirant efficacy and wash-off.

All exemplified amounts are weight percentages based upon the total weight of the antiperspirant stick composition, unless otherwise specified.

Examples 1–3

The Tables 1–3 examples are each prepared as follows. First, the gellants (fully hydrogenated HEAR and C18–C36 acid triglyceride) are dissolved into the silicone liquids, cyclopentasiloxane and dimethicone, by heating the gellants and silicone materials together while stirring on an IKA stir plate to 85° C. The solid antiperspirant active is then added slowly with agitation to the heated mixture, and once added, the resulting mixture is allowed to reheat to 85° C. At this point the water soluble solids (e.g., calcium pantothenate) are added along with the Panthenyl Triacetate. The mixture is milled at 4 on the speed setting using an IKA brand T 25 Ultra-Turrax disperser using the S 25 N-25F attachment. The product is milled for a period of time sufficient to reduce and break up any agglomerates of solid water-soluble solids and or solid antiperspirant active. To measure when sufficient milling has occurred, a small sample of milled product is withdrawn from the hot mixture on a metal spatula and examined under a polarizing microscope. Product is milled until no visible agglomerates greater than 10 microns of water-soluble solids and or antiperspirant active are evident. Once milling is completed, then the product is cooled and poured at approximately 60° C. into antiperspirant containers, where it is allowed to cool to ambient temperatures to the desired product form. Example 1.3 is also formulated with 3% petrolatum with a corresponding reduction in cyclopentasiloxane concentration, and then applied by the methods of the present invention.

TABLE 1

Antiperspirant Soft Solids/Creams

| Ingredients | Example 1.1 | Example 1.2 | Example 1.3 | Example 1.4 |
|---|---|---|---|---|
| Al Zr Trichlorohydrex Glycinate (solid) | 25.25 | 25.25 | 25.25 | 25.25 |
| Dimethicone (10 cs) | 5.00 | 5.00 | 5.00 | 5.00 |
| Fully Hydrogenated High Erucic Acid Rapeseed oil (HEAR oil) | 5.00 | 5.00 | 5.00 | 5.00 |
| White Petrolatum U.S.P. Grade* | 0.20 | 0.50 | 0.90 | 0.50 |
| C-18–36 Acid Triglyceride Syncrowax HGLC | 1.25 | 1.25 | 1.25 | 1.25 |
| Perfume | 0.75 | 0.75 | 0.75 | 0.75 |
| Calcium Pantothenate (solid) | 0.50 | 0 | 0 | 3.00 |
| Panthenyl Triacetate | 0.50 | 3.00 | 0 | 0 |
| Cyclopentasiloxane | QS | QS | QS | QS |
| Total | 100.00 | 100.00 | 100.00 | 100.00 |

*Super White Protopet manufactured by Witco

TABLE 2

Antiperspirant Wax Sticks (Solid)

| Ingredients | Example 2.1 | Example 2.2 | Example 2.3 | Example 2.4 |
|---|---|---|---|---|
| Al Zr Trichlorohydrex Glycinate (solid) | 20.00 | 20.00 | 20.00 | 20.00 |
| Stearyl Alcohol | 11.00 | 11.00 | 11.00 | 11.00 |
| Talc, USP Grade | 6.50 | 7.00 | 7.50 | 3.00 |
| White Petrolatum U.S.P. Grade* | 0.20 | 0.50 | 0.90 | 0.50 |
| Dimethicone (50 cs) | 3.00 | 5.00 | 5.00 | 5.00 |
| Castor Wax | 2.90 | 5.00 | 5.00 | 5.00 |
| Calcium Pantothenate (solid) | 0.50 | 0 | 0 | 3.00 |
| Panthenyl Triacetate | 0.50 | 3.00 | 0 | 0 |
| Fumed Silica | 0.18 | 0.18 | 0.18 | 0.18 |
| Dipropylene Glycol | 0.18 | 0.18 | 0.18 | 0.18 |
| Microthene | 0.18 | 0.18 | 0.18 | 0.18 |
| Behenyl Alcohol | 0.08 | 0.08 | 0.08 | 0.08 |
| Perfume | 0.75 | 0.75 | 0.75 | 0.75 |
| Cyclopentasiloxane | QS | QS | QS | QS |
| Total | 100.00 | 100.00 | 100.00 | 100.00 |

TABLE 3

Antiperspirant Low Sticks (Solid) Residue

| Ingredients | Example 3.1 | Example 3.2 | Example 3.3 | Example 3.4 |
|---|---|---|---|---|
| Al Zr Trichlorohydrex Glycinate (solid) | 25.25 | 20.00 | 20.00 | 20.00 |
| Dimethicone (50 cs) | 5.00 | 5.00 | 5.00 | 5.00 |
| Fully Hydrogenated High Erucic Acid Rapeseed oil (HEAR oil) | 15.00 | 15.00 | 15.00 | 15.00 |
| Isopar M | 10.00 | 10.00 | 10.00 | 10.00 |
| White Petrolatum U.S.P. Grade* | 0.20 | 0.50 | 0.90 | 0.50 |
| C-18–36 Acid Triglyceride Syncrowax HGLC | 3.75 | 3.75 | 3.75 | 3.75 |
| Perfume | 0.75 | 0.75 | 0.75 | 0.75 |
| Calcium Pantothenate (solid) | 0.50 | 0 | 0 | 3.00 |
| Panthenyl Triacetate | 0.50 | 3.00 | 0 | 0 |
| Cyclopentasiloxane | QS | QS | QS | QS |
| Total | 100 | 100 | 100 | 100 |

Example 4

Antiperspirant Aerosols

The Table 4 examples of aerosol embodiments can be prepared by methods well know for making aerosol antiperspirant products, such as those methods described in U.S. Pat. No. 6,136,303 (Ruebusch et al.); U.S. Pat. No. 4,904,463 (Johnson et al.) and U.S. Pat. No. 4,840,786 (Johnson et al.). The Table 4 examples can be prepared by combining the water-soluble solids (e.g., calcium pantothenate, etc.) with the solid antiperspirant active in an aerosol container. All other materials are mixed together to form a homogeneous premix liquid before adding the newly formed premix to the aerosol container. The propellant is then added, under pressure, and the container sealed.

TABLE 4

Antiperspirant Aerosols

| Ingredients | Example 4.1 | Example 4.2 | Example 4.3 | Example 4.4 |
|---|---|---|---|---|
| 5/6 Aluminum chlorohydrate solid (Macrospherical-95) Reheis Chemical Company | 10.50 | 10.50 | 11.00 | 10.50 |
| SE76 Silicone Gum[1] | 5.00 | 5.00 | 5.00 | 5.00 |
| SWS 801[2] | 15.00 | 15.00 | 15.00 | 15.00 |
| Cyclomethicone[3] | 3.40 | 3.40 | 3.40 | 3.40 |
| White Petrolatum U.S.P. Grade* | 0.05 | 0.10 | 0.30 | 0.50 |
| Panthenyl Triacetate | 0.20 | 0.50 | 0 | 0 |
| Tocopherol Acetate | 0.50 | 0 | 0 | 0.50 |
| Propellant A-46[4] | QS | QS | QS | QS |
| Total | 100.00 | 100.00 | 100.00 | 100.00 |

[1]Silicone gum pre-mix (15% silicone - 15 x $10^6$ centipoise and 85% cylomethicone); General Electric Company
[2]Diamino-functional silicone, m.w. 76,000; SWS Silicone, inc.
[3]Total cyclomethicone, including that contained in the silicone premix described in note 2.
[4]Mixture of 87% Isobutane and 13% propane (by weight of total propellant)

Example 5

Antiperspirant Liquids

The Table 5 examples are each prepared by combining and mixing together the various components under ambient conditions. Each of the resulting mixtures is then milled on a IKA brand T 25 Ultra-Turrax disperser (4 speed setting) using the S 25 N-25F attachment. The mixture is subjected to the milling process long enough to reduce and break up any water-soluble solids and or antiperspirant active agglomerates. The mixture is sufficiently milled when a small sample as examined under a polarizing microscope shows no visible agglomerates greater than 10 microns. Once milling is complete, the liquid antiperspirant product is poured into roll-on antiperspirant containers, or other suitable liquid antiperspirant dispenser.

TABLE 5

Antiperspirant Liquids

| Ingredients | Example 5.1 | Example 5.2 | Example 5.3 | Example 5.4 |
|---|---|---|---|---|
| Al Zr Trichlorohydrex Glycinate (solid) | 21.25 | 21.25 | 21.75 | 20.00 |
| Dimethicone (10 cs) | 10.00 | 10.00 | 10.00 | 10.00 |
| Microthene | 7.00 | 7.00 | 7.00 | 7.00 |
| Bentone 38 | 1.00 | 1.00 | 1.00 | 1.00 |
| Cab-O-Sil | 0.70 | 0.70 | 0.70 | 0.70 |
| Propylene Carbonate | 0.30 | 0.30 | 0.30 | 0.30 |
| Perfume | 0.50 | 0.50 | 0.50 | 0.50 |
| White Petrolatum U.S.P. Grade* | 0.20 | 0.50 | 0.90 | 0.50 |
| Panthenyl Triacetate | 0.50 | 3.00 | 0 | 0 |
| Ethyl Panthenyl | 0 | 0 | 1.50 | 0 |
| Tocopherol Acetate | 0 | 0.50 | 0 | 0 |
| Cyclopentasiloxane | QS | QS | QS | QS |
| Total | 100.00 | 100.00 | 100.00 | 100.00 |

What is claimed is:

1. Antiperspirant compositions comprising:
   (a) from about 0.1% to about 30% by weight of an antiperspirant active;
   (b) from about 0.05% to about 0.95% by weight of petrolatum;
   (c) from about 10% to about 99% by weight of a liquid carrier; and
   (d) from about 0.1% to about 30% by weight of a suspending agent.

2. An antiperspirant composition according to claim 1, wherein petrolatum concentration ranges from about 0.3% to about 0.8% by weight of the composition.

3. An antiperspirant composition according to claim 1, wherein the petrolatum comprises White Petroleum U.S.P.

4. An antiperspirant composition according to claim 3, wherein the petrolatum has a Saybolt Viscosity of at least about 55.

5. An antiperspirant composition according to claim 1 wherein the composition is anhydrous and contains less than 5% by weight of free or added water.

6. An antiperspirant composition according to claim 1 wherein the antiperspirant active is selected from the group consisting of zirconium-containing active, aluminum-containing active, and combinations thereof.

7. An antiperspirant composition according to claim 4 wherein the antiperspirant active is selected from the group consisting of aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered, and combinations thereof.

8. An antiperspirant composition according to claim 5, wherein the antiperspirant active comprises a zirconium-containing active and an aluminum-containing active, at a combined concentration of from about 5% to about 30% by weight of the composition.

9. An antiperspirant composition according to claim 6 wherein the carrier comprises a volatile cyclomethicone that represents from about 5% to about 80% by weight of the composition.

10. An antiperspirant composition according to claim 7, wherein the carrier further comprises a non-volatile silicone liquid that represents from about 1% to about 35% by weight of the composition.

11. An antiperspirant composition according to claim 1, wherein the antiperspirant active is in the form of solid particulates.

12. An antiperspirant composition according to claim 1, wherein the composition further comprises from about 3% to about 35% by weight of a suspending agent.

13. An antiperspirant composition according to claim 10, wherein the composition is in the form of a solid stick.

14. An antiperspirant composition according to claim 10, wherein the composition is in the form of a soft solid.

15. An antiperspirant composition according to claim 10, wherein the suspending agent comprises hydrogenated castor oil.

16. An antiperspirant composition according to claim 1, wherein the composition further comprises from about 0.1% to about 10% by weight of PEG-8 distearate.

17. An antiperspirant composition according to claim 1, wherein the composition further comprises from about 0.1% to about 5% by weight of silica.

18. An antiperspirant composition according to claim 1, wherein the composition further comprises from about 0.1% to about 10% by weight of C18–36 triglycerides.

19. A method of improving antiperspirant efficacy, said method comprising the topical underarm application of the composition of claim 1.

20. A method of improving antiperspirant wash-off, said method comprising the topical underarm application of the composition of claim 1.

21. A method of inhibiting underarm perspiration wetness and odor, said method comprising the topical underarm application of the composition of claim 1.

* * * * *